United States Patent
Israels et al.

(10) Patent No.: US 9,137,984 B2
(45) Date of Patent: Sep. 22, 2015

(54) SEED TREATMENT COMPOSITIONS AND METHODS

(75) Inventors: Rafel Israels, Cologne (DE); Katharine Klamczynski, Boehl-Iggelheim (DE); Matthias Bratz, Maxdorf (DE); Ulf Schlotterbeck, Mannheim (DE); Dirk Voeste, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 12/672,751

(22) PCT Filed: Aug. 14, 2008

(86) PCT No.: PCT/EP2008/060672
§ 371 (c)(1),
(2), (4) Date: Feb. 9, 2010

(87) PCT Pub. No.: WO2008/021985
PCT Pub. Date: Feb. 19, 2009

(65) Prior Publication Data
US 2011/0166022 A1    Jul. 7, 2011

(30) Foreign Application Priority Data
Aug. 16, 2007  (EP) ..................................... 07114462

(51) Int. Cl.
| | | |
|---|---|---|
| *A01N 25/30* | (2006.01) | |
| *A01N 43/653* | (2006.01) | |
| *A01N 43/48* | (2006.01) | |
| *A01N 25/00* | (2006.01) | |
| *A01N 25/04* | (2006.01) | |
| *A01N 47/02* | (2006.01) | |
| *A01N 47/24* | (2006.01) | |
| *A01N 53/00* | (2006.01) | |

(52) U.S. Cl.
CPC ................ *A01N 25/00* (2013.01); *A01N 25/04* (2013.01); *A01N 25/30* (2013.01); *A01N 43/653* (2013.01); *A01N 47/02* (2013.01); *A01N 47/24* (2013.01); *A01N 53/00* (2013.01)

(58) Field of Classification Search
CPC ... A01N 25/00; A01N 25/04; A01N 2300/00; A01N 43/653; A01N 47/02; A01N 47/24; A01N 53/00; A01N 25/30
See application file for complete search history.

(56) References Cited

U.S. PATENT DOCUMENTS

| | | | |
|---|---|---|---|
| 6,455,471 B1 | 9/2002 | Gubelmann-Bonneau et al. | |
| 6,547,867 B2 * | 4/2003 | Rogols et al. .............. | 106/134.1 |
| 2002/0040044 A1 * | 4/2002 | Schlatter ....................... | 514/383 |
| 2007/0053944 A1 | 3/2007 | Vermeer | |

FOREIGN PATENT DOCUMENTS

| | | |
|---|---|---|
| EP | 0 951 831 | 10/1999 |
| WO | WO 95/07614 | 3/1995 |
| WO | WO 00/35284 | 6/2000 |
| WO | WO 02/19821 | 3/2002 |
| WO | WO 2005/036963 | 4/2005 |
| WO | WO 2005/089546 | 9/2005 |
| WO | WO 2006/035316 | 4/2006 |
| WO | WO 2007/003319 | 1/2007 |
| WO | WO 2007039080 A1 * | 4/2007 |
| WO | WO 2008/061899 | 5/2008 |
| WO | WO 2008/136917 | 11/2008 |

OTHER PUBLICATIONS

Hess et al., Weed Technology, 2000, 14, 807-813.*
Wang et al., Pesticide Biochemistry and Physiology, 2007, 87, 1-8.*
Simmen et al., Crop Protection, 1996, 15(3), 275-281.*
International Search Report and Written Opinion dated Nov. 16, 2009, in International Application No. PCT/EP2008/060672, filed Aug. 14, 2008.

* cited by examiner

*Primary Examiner* — Abigail Fisher
(74) *Attorney, Agent, or Firm* — Brinks Gilson & Lione

(57) ABSTRACT

The invention relates to seed treatment compositions comprising active ingredient, polyarylphenol polyalkoxy ether phosphate and/or polyarylphenol polyalkoxy ether sulphate, and copolymer having polyalkoxy ether side chains.
The polyarylphenol polyalkoxy ether phosphate and/or the polyarylphenol polyalkoxy ether sulphate in combination with the copolymer having polyalkoxy ether side chains are used as dispersant, especially to provide a dispersion of suspended active ingredient.
The present invention also relates to methods of treating seed with such a composition.

24 Claims, No Drawings

SEED TREATMENT COMPOSITIONS AND METHODS

This application is a National Stage application of International Application No. PCT/EP2008/060672 filed Aug. 14, 2008, the entire contents of which is hereby incorporated herein by reference. This application also claims the benefit under 35 U.S.C. §119 of European Patent Application No. 07114462.0 filed Aug. 16, 2007, the entire contents of which is hereby incorporated herein by reference.

The invention relates to seed treatment compositions and methods of treating seed. The invention also relates to the use of polyarylphenol polyalkoxy ether phosphates and/or polyarylphenol polyalkoxy ether sulfates as well as of copolymers having polyalkoxy ether side chains in seed treatment compositions.

Seed treatment is the process of applying active ingredients to seeds in order to support the germination and/or the growth of a large variety of crops. Typical examples include the application of pesticides such as fungicides, insecticides and plant growth regulators, as well as other active ingredients such as fertilizers.

Being an alternative to traditional broadcast spraying of pesticides, seed treatment compositions must fulfil a number of special requirements which include their applicability to seeds in commercial equipment, the adhesion of the active ingredients to the treated seeds, and good flowability of the treated seeds. Of course, the treated seeds must still be capable of germination.

A number of compositions widely used for seed treatment are dispersions. Such compositions require one or more dispersants to lower the viscosity and to stabilize the dispersion against agglomeration and crystal growth.

WO 2005/036963 describes suspension concentrates comprising an azole and/or a strobilurine, a penetration promoter from the alkanol alkoxylate group, a dispersant, water, and optionally further auxiliaries. The dispersant is a polymerisate of 2-methyl-2-propenoic acid methyl ether and α-(2-methyl-1-oxo-2-propenyl)-ω-methoxy-poly-(oxy-1,2-ethanediyl) or a tristyrylphenol-ethoxylate and/or a propylene oxide-ethylene oxide block copolymer with a molecular weight from 8.000 to 10.000. The compositions are said to be useful for treating plants, seed and soil.

Although the use of dispersants in seed treatment compositions is well-known in the art, the commonly used dispersants tend to provide seed treatment compositions which are not entirely satisfactory. It is especially the combination of seed-specific and general requirements for seed treatment compositions that remains hard to achieve.

An object of the present invention was to provide a seed treatment composition that is capable of forming a stable dispersion and suitable for seed treatment.

Surprisingly, it has now been found that a combination of a polyarylphenol polyalkoxy ether phosphate and/or a polyarylphenol polyalkoxy ether sulfate with a copolymer having polyalkoxy ether side chains forms an excellent dispersing system for a large number of agrochemicals in seed treatment compositions.

The invention therefore relates to seed treatment compositions comprising active ingredient, polyarylphenol polyalkoxy ether phosphate and/or polyarylphenol polyalkoxy ether sulphate, and copolymer having polyalkoxy ether side chains. Particular embodiments of the compositions are defined in the claims and disclosed herein.

The compositions of the present invention show a stable particle size of dispersed, in particular suspended, active ingredient(s).

As used herein, a "composition" comprises at least one active ingredient and at least one auxiliary agent.

As used herein, ingredients comprise active ingredients and auxiliary agents.

In the present invention, an "active ingredient" is a compound which directly exerts a biologically relevant effect, preferably a pesticidal effect as described herein.

The term "auxiliary agent" refers to a compound or combination of compounds which do not exert a biologically relevant effect of their own, but support the effects of the active ingredient(s). When auxiliary agents are used, their choice will depend on the active ingredients and on the procedures selected for seed treatment.

Usually, the compositions thus comprise an active ingredient component ("A") and an auxiliary agent component ("B"). The active ingredient component ("A") of the composition comprises one or more than one active ingredient(s). The auxiliary agent component ("B") comprises one or more auxiliary agent(s).

As used herein, the term "at least one" refers to 1, 2, 3, or more members from a group and includes mixtures of 2, 3, or more different members from the group.

Unless indicated otherwise, all amounts in % by weight refer to the weight of the total composition (or formulation).

In general, the compositions comprise from 0.005% by weight to 95% by weight, preferably from 0.01% by weight to 90% by weight, in particular from 0.1 or 0.5% by weight to 50% by weight, of the active ingredient component "A", the balance being formed by component "B". In this context, the active ingredients are employed in a purity of 90% to 100%, preferably 95% to 100% (according to NMR spectrum).

According to the invention, the active ingredient is especially selected from plant protection active agents (pesticides). Such an agent has the purpose or effect of preventing infection of a plant by any pest or of repelling, deterring or destroying the pest or of reducing in another way the damage caused by it. Plant pests can belong to different groups of organisms; the higher animals, in particular insects and acarids, include numerous important pests, as do nematodes and snails; vertebrates, such as mammals and birds, are today of secondary importance in industrialized countries. Numerous groups of microbes, including fungi, bacteria, inclusive of mycoplasmas, viruses and viroids, comprise pests, and even weeds, which compete with useful plants for limited habitat and other resources, can be classed as pests in the broad sense. Pesticides comprise in particular aphicides, acaricides, desiccants, bactericides, chemosterilants, defoliants, antifeedants, fungicides, herbicides, herbicide safeners, insect attractants, insecticides, insect repellents, molluscicides, nematicides, mating disrupters, plant activators, plant growth regulators, rodenticides, mammal repellents, synergists, bird repellents and virucides.

The following list of pesticides which can be used according to the invention, is intended to illustrate the possible active ingredients, but not to impose any limitation:

A. Insecticides and Acaricides

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, gamma-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula (I¹)

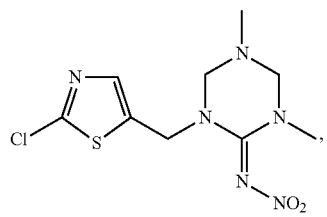

(I¹)

A.6. GABA antagonist compounds: acetoprole, endosulfan, ethiprole, fipronil, vaniliprole, pyrafluprole, pyriprole, the phenylpyrazole compound of formula (I²)

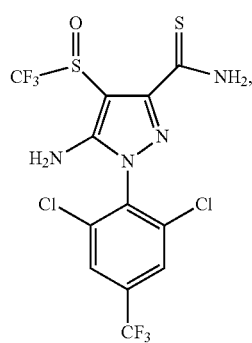

(I²)

A.7. Macrocyclic lactone insecticides: abamectin, emamectin, milbemectin, lepimectin, spinosad, the compound of formula (I³) (CAS No. 187166-40-1)

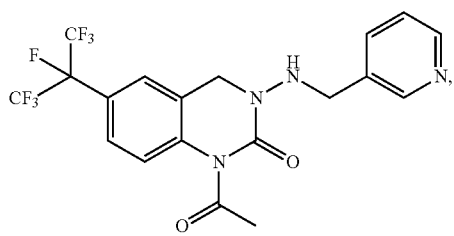

(I³)

A.8. METI I compounds: fenazaquin, pyridaben, tebufenpyrad, tolfenpyrad, flufenerim;
A.9. METI II and III compounds: acequinocyl, fluacyprim, hydramethylnon;
A.10. Uncoupler compounds: chlorfenapyr;
A.11. Oxidative phosphorylation inhibitor compounds: cyhexatin, diafenthiuron, fenbutatin oxide, propargite;
A.12. Moulting disruptor compounds: cyromazine;
A.13. Mixed Function Oxidase inhibitor compounds: piperonyl butoxide;
A.14. Sodium channel blocker compounds: indoxacarb, metaflumizone;
A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula (I⁴)

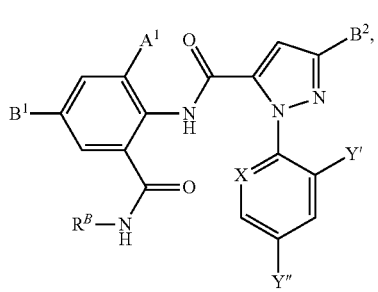

(I⁴)

N—R'-2,2-dihalo-1-R"cyclo-propanecarboxamide-2-(2,6-dichloro-α,α,α-tri-fluoro-ptolyl)hydrazone or N—R'-2,2-di(R''')propionamide-2-(2,6-dichloro-α,α,α-trifluoro-p-tolyl)hydrazone, wherein R' is methyl or ethyl, halo is chloro or bromo, R" is hydrogen or methyl and R''' is methyl or ethyl, anthranilamide compounds of formula (I⁵)

wherein $A^1$ is $CH_3$, Cl, Br, I, X is C—H, C—Cl, C—F or N, Y' is F, Cl, or Br, Y" is H, F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$.

The commercially available compounds of the group A may be found in The Pesticide Manual, 13$^{th}$ Edition, British Crop Protection Council (2003) among other publications. Thioamides of formula ($I'^2$) and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamides of formula ($r^5$) and their preparation have been described in WO 01/70671; WO 02/48137; WO 03/24222, WO 03/15518, WO 04/67528; WO 04/33468; and WO 05/118552. The malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$ have been described in WO 05/63694.

B. Fungicides:

B.1. Strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-((2,5-dimethylphenyloxymethylene)phenyl)-3-methoxyacrylate;

B.2. Carboxamides such as
  carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
  carboxylic acid morpholides: dimethomorph, flumorph;
  benzamides: flumetover, fluopicolide (picobenzamid), zoxamide;
  other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

B.3. Azoles such as
  triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
  imidazoles: cyazofamid, imazalil, pefurazoate, prochloraz, triflumizole;
  benzimidazoles: benomyl, carbendazim, fuberidazole, thiabendazole;
  others: ethaboxam, etridiazole, hymexazole;

B.4. Nitrogenous heterocyclyl compounds such as
  pyridines: fluazinam, pyrifenox, 3-[5-(4-chlorophenyl)-2,3-dimethylisoxazolidin-3-yl]-pyridine;
  pyrimidines: bupirimate, cyprodinil, ferimzone, fenarimol, mepanipyrim, nuarimol, pyrimethanil;
  piperazines: triforine;
  pyrroles: fludioxonil, fenpiclonil;
  morpholines: aldimorph, dodemorph, fenpropimorph, tridemorph;
  dicarboximides: iprodione, procymidone, vinclozolin;
  others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

B.5. Carbamates and dithiocarbamates such as
  dithiocarbamates: ferbam, mancozeb, maneb, metiram, metam, propineb, thiram, zineb, ziram;
  carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

B.6. Other fungicides such as
  guanidines: dodine, iminoctadine, guazatine;
  antibiotics: kasugamycin, polyoxins, streptomycin, validamycin A;
  organometallic compounds: fentin salts;
  sulfur-containing heterocyclyl compounds: isoprothiolane, dithianon;
  organophosphorus compounds: edifenphos, fosetyl, fosetyl-aluminum, iprobenfos, pyrazophos, tolclofos-methyl, phosphorous acid and its salts;
  organochlorine compounds: thiophanate-methyl, chlorothalonil, dichlofluanid, tolylfluanid, flusulfamide, phthalide, hexachlorbenzene, pencycuron, quintozene;
  nitrophenyl derivatives: binapacryl, dinocap, dinobuton;

inorganic active compounds: Bordeaux mixture, copper acetate, copper hydroxide, copper oxychloride, basic copper sulfate, sulfur;

others: spiroxamine, cyflufenamid, cymoxanil, metrafenone.

C. Herbicides:

C.1 Lipid biosynthesis inhibitors such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

C.2 ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

C.3 Photosynthesis inhibitors such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

C.4 Protoporphyrinogen-IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipraclofen and etnipromid;

C.5 Bleacher herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl)pyrimidine, and also 3-heterocyclyl-substituted benzoyl derivatives of the formula II (see in WO 96/26202, WO 97/41116, WO 97/41117 and WO 97/41118)

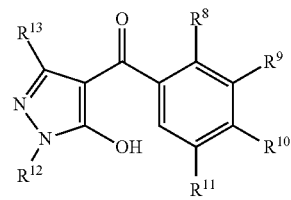

in which the variables $R^8$ to $R^{13}$ are as defined below:

$R^8$, $R^{19}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of such as thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetra-substituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

C.7 EPSP synthase inhibitors such as glyphosate;

C.8 glutamine synthase inhibitors such as glufosinate and bilanaphos;

C.9 DHP synthase inhibitors such as asulam;

C.10 Mitose inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

C.11 VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

C.12 Cellulose biosynthesis inhibitors such as dichlobenil, chlorthiamid, isoxaben and flupoxam;

C.13 Decoupler herbicides such as dinofenate, dinoprop, dinosam, dinoseb, dinoterb, DNOC, etinofen and medinoterb;

C.14 Auxin herbicides such as clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

C.15 Auxin transport inhibitors such as naptalam, diflufenzopyr;

C.16 Benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

D. Safeners:

Benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloroacetyl)-1-oxa-4-azaspiro [4.5]decane (AD-67; MON 4660) and oxabetrinil Preferred insecticides are selected from:

acetamiprid, alpha-cypermethrin, beta-cypermethrin, bifenthrin, carbofuran, carbosulfan, clothianidin, cyclopro-thrin, cyfluthrin, cypermethrin, deltamethrin, diflubenzuron, dinotefuran, etofenprox, fenbutatin-oxide, fenpropathrin, fipronil, flucythrinate, imidacloprid, lambda-cyhalothrin, nitenpyram, pheromones, spinosad, teflubenzuron, tefluthrin, terbufos, thiacloprid, thiamethoxam, thiodicarb, tralomethrin, triazamate, zeta-cypermethrin, spirotetramat, flupyrazofos, NC 512, tolfenpyrad, flubendiamide, bistrifluoron, benclothiaz, DPX-E2Y45, HGW86, pyrafluprole, pyriprole, F-7663, F-2704, amidoflumet, flufenerim, cyflumetofen. Particular preference is given to clothianidin, fipronil, imidacloprid and thiamethoxam.

Preferred fungicides are selected from:

metalaxyl, oxadixyl, guazatine, pyrimethanil, streptomycin, difenoconazole, epoxiconazole, fluquiconazole, flutriafol, hymexazole, imazalil, metconazole, prochloraz, prothioconazole, tebuconazole, thiabendazole, triadimenol, triticonazole, iprodion, maneb, mancozeb, metiram, thiram, benomyl, boscalid, carbendazim, carboxin, dazomet, silthiofam, copper fungicides, fludioxonil, sulfur, dazomet, azoxystrobin, kresoxim-methyl, orysastrobin, pyraclostrobin, trifloxystrobin, captan dimethomorph. Particular preference is given to pyraclostrobin, triticonazole and fluquinconazole.

A particular embodiment of the invention relates to seed treatment compositions comprising pyraclostrobin and triticonazole.

In a particular embodiment of the invention, the seed treatment composition may comprise one or more repellents for warm-blooded animals, e.g. birds, dogs and hedgehogs, for example nonanoic acid vanillyl amide. The amount of repellent will preferably range from 0.1 to 5% by weight, based on the total weight of the composition.

Polyarylphenol polyalkoxy ether phosphates and polyarylphenol polyalkoxy ether sulfates are known per se. A polyarylphenol polyalkoxy ether sulfate, for instance, is sold under the tradename Soprophor® 4D384 or TERSPERSE 2218® (CAS registry number: 119432-41-6); a polyarylphenol polyalkoxy ether phosphate, for instance, is sold under the tradename Soprophor® FLK (CAS registry number: 176776-21-9).

Preferably, the polyarylphenol polyalkoxy ether phosphates and sulfates are tristyrylphenol polyalkoxy ether sulfates and phosphates having the formula (I):

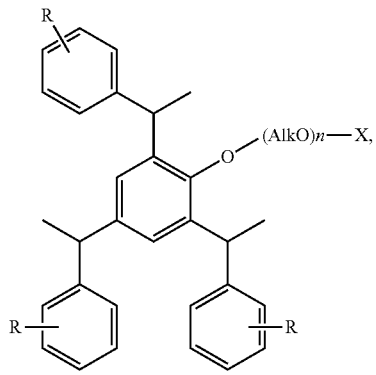

wherein each R independently represents hydrogen or $C_1$-$C_4$ alkyl; Alk represents $C_2$-$C_6$ alkylene; n has a value from 5 to 60; and X is —$SO_3H_2$ or —$PO_3H$; or an agriculturally acceptable base addition salt thereof.

The phosphate or the sulfate can be used in its protonated (fee acid) form. Preferably, it is a base addition salt comprising an agriculturally acceptable cation such as an alkali metal cation, preferably a lithium, sodium and potassium cation; an alkaline earth metal cation, preferably a calcium, magnesium and barium cation; a transition metal cation, preferably a manganese, copper, zinc and iron cation; the ammonium cation; a positively ionized amine, preferably an ammonium cation carrying one to four $C_{1-4}$ alkyl substituents or one phenyl or benzyl substituent in addition to zero to three $C_{1-4}$ alkyl substituents, more preferably the diisopropylammonium, tetramethylammonium, trimethylbenzylammonium and tetrabutylammonium cation; a phosphonium cation; a sulfonium cation, preferably a tri($C_{1-4}$-alkyl)sulfonium cation; and a sulfoxonium cation, preferably a tri($C_{1-4}$-alkyl) sulfoxonium cation. Here the term "$C_{1-4}$ alkyl" is used to refer to a saturated linear or branched hydrocarbon radical having 1 to 4 carbon atoms, e.g. methyl, ethyl, propyl, methylethyl, butyl, 1-methylpropyl, 2-methylpropyl or dimethylethyl. Particular preference is given to metal cations and the ammonium cation.

The alkoxylation results from the reaction with one or more than one suitable alkylene oxide(s) generally exhibiting 2 to 6 and preferably 2 or 3 carbon atoms. These include in particular 1,2-ethylene oxide (EO), 1,2-propylene oxide (PO), 1,2-butylene oxide (BO), 1,2-pentylene oxide (PeO) or 1,2-hexylene oxide (HO). Particular preference is given to 1,2-ethylene oxide (EO).

The degree of alkoxylation resulting in each case depends on the amounts of alkylene oxide(s) used for the reaction and on the reaction conditions. In this connection, it is generally a statistical mean value since the number of alkylene oxide units per polyarylphenol molecule resulting from the reaction varies.

The degree of alkoxylation, i.e. the mean chain length of the polyether chains (i.e., the value of n) can be controlled by the molar ratio of polyarylphenol to alkylene oxide and the reaction conditions used for preparing the polyalkoxylates. The polyalkoxy ether moieties usually have more than 5, preferably more than 10, and in particular more than 15 alkylene oxide units. Usually, it has not more than 60, preferably not more than 50 and in particular not more than 40 alkylene oxide units. Preference is given to polyarylphenol polyalkoxy ether phosphates and polyarylphenol polyalkoxy ether sulfates which have 5 to 30, preferably 10 to 20 and in particular 14 to 18 alkylene oxide units.

According to a particular embodiment, the seed treatment composition comprises at least 0.1% by weight, preferably at least 0.5% by weight and in particular at least 1% by weight of polyarylphenol polyalkoxy ether phosphate and/or sulfate.

According to a further particular embodiment, the seed treatment composition comprises at most 50% by weight, preferably at most 20% by weight and in particular at most 5% by weight of polyarylphenol polyalkoxy ether phosphate and/or sulfate.

According to one aspect, the weight ratio of polyarylphenol polyalkoxy ether phosphate and/or polyarylphenol polyalkoxy ether sulfate to solid active ingredient(s) is at least 1:1, preferably at least 5:1, and in particular at least 10:1.

According to another aspect, the weight ratio of polyarylphenol polyalkoxy ether phosphate and/or polyarylphenol polyalkoxy ether sulfate to solid active ingredient(s) is at most 500:1, preferably at most 100:1, and in particular at most 50:1.

Copolymers having polyalkoxy ether side chains are also known per se. A copolymer based on methacrylic esters, for instance, is sold under the tradename Atlox® 4913 or TER-SPERSE® 2500 (CAS registry number: 111740-364).

The copolymer having polyalkoxy ether side chains usually comprises one monomer unit to which the polyalkoxy ether side chain is attached and, optionally, one or more additional monomer units of copolymerizable comonomers.

According to a particular embodiment of the present invention, the copolymer comprises
(i) monomer units of at least one ester of an ethylenically unsaturated carboxylic acid, wherein the carboxylic acid ester has an alkoxylate residue of the general formula (II):

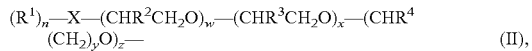

$$(R^1)_n\text{—}X\text{—}(CHR^2CH_2O)_w\text{—}(CHR^3CH_2O)_x\text{—}(CHR^4(CH_2)_yO)_z\text{—} \quad (II),$$

in which
$R^1$ is hydrogen or an aliphatic hydrocarbon residue with 1 to 40 carbon atoms, preferably linear or branched, saturated or unsaturated $C_1$-$C_6$-alkyl;
$R^2$, $R^3$, $R^4$ are, independently of one another, hydrogen or $C_1$-$C_4$-alkyl;
w, x, z correspond, independently of one another, to a value of 0 to 100, the sum of w, x and z being greater than 0;
y corresponds to a value of 1 to 20; and
X is N or O,
n being 1 if X is O; or n being 2 if X is N; and
(ii) monomer units of at least one additional copolymerizable comonomer.

The term "monomer unit" means, in the context of the present disclosure, a monomer which has been incorporated in the copolymer, where the monomer which has been incorporated in the copolymer, i.e. the monomer unit, in comparison with the actual monomer charged to the polymerization reaction, is not only structurally changed by the polymerization reaction but, in addition, can also exhibit further modifications. Thus, in particular, the monomer units of the carboxylic acid esters can be derived by esterification from the monomers charged to the reaction.

The carboxylic acid esters exhibit, as alcohol part, alkoxylates of linear or branched, saturated or unsaturated, primary, secondary or tertiary alcohols or amines of formula (II). These alkoxylates correspond to the polyalkoxy ether side chains of the copolymer.

According to a preferred embodiment, X is oxygen (alcohol alkoxylates).

Particular embodiments of alkoxylates of the formula (II) ensue if z corresponds to a value of 1 to 100 and w and x are zero (alkoxylates, such as ethoxylates ($R^4$=H; y=1) or propoxylates ($R^4$=$CH_3$; y=1)); if w is zero and x and z correspond, independently of one another, to a value of 1 to 100 (EO/PO block alkoxylates with, for example, an EO-PO block arrangement (y=1; $R^3$=$CH_3$; $R^4$=H) or a PO-EO block arrangement (y=1; $R^3$=H; $R^4$=$CH_3$)); if w, x and z correspond, independently of one another, to a value of from 1 to 100 (EO/PO/EO block alkoxylates with, for example, an EO-PO-EO block arrangement (y=1; $R^2$=H; $R^3$=$CH_3$; $R^4$=H) or a PO-EO-PO block arrangement (y=1; $R^2$=$CH_3$; $R^3$=H; $R^4$=$CH_3$)).

Alcohol residues of the formula (II) in which $R^1$ is an alkyl residue with preferably 1 to 6 carbon atoms (if X=O), or in which one $R^1$ is an alkyl residue with preferably 1 to 6 carbon atoms and the other is hydrogen (if X=N) have proved in particular to be suitable according to the invention.

Ethoxylate residues of the formula (IIa)

$$R^1\text{—}O(C_2H_4O)_z\text{—} \quad (IIa)$$

in which
$R^1$ has the above meaning and preferably is linear or branched, saturated or unsaturated $C_1$-$C_6$ alkyl; and
z corresponds to a value of 1 to 100 and preferably lies between 1 and 30,
are very particularly suitable.

Consequently, $R^1$ represents in particular one of the following alkyl residues: methyl, ethyl, n-propyl, iso-propyl.

The alkoxylation results from the reaction with suitable alkylene oxides, which generally exhibit 2 to 15 and preferably 2 to 6 carbon atoms. Mention may in particular be made here of 1,2-ethylene oxide (EO), 1,2-propylene oxide (PO), 1,2-butylene oxide (BO), 1,2-pentylene oxide (PeO) and 1,2-hexylene oxide (HO).

The degree of alkoxylation resulting in each case depends on the amounts of alkylene oxide(s) used for the reaction and on the reaction conditions. In this connection, it is generally a statistical mean value since the number of alkylene oxide units of the alcohol alkoxylate residues resulting from the reaction varies.

The degree of alkoxylation, i.e. the mean chain length of the polyether chains of suitable alkoxylate residues, can be controlled by the molar quantitative proportion of alcohol or amine to alkylene oxide used for preparing the alkoxylates. Alkoxylates with approximately 1 to 50, preferably approximately 1 to 20, in particular 1 to 10 alkylene oxide units (sum of w, x, z), in particular ethylene oxide units, are preferred.

Preferably, the ethylenically unsaturated carboxylic acid esters have 4 to 8 and in particular 4 to 6 carbon atoms in the carboxylic acid part.

Mention may in particular be made of (meth)acrylic acid esters. Among these carboxylic acid esters, methacrylic acid esters are particularly preferred.

It should be mentioned at this point that the expression "(meth)acrylic" represents both "acrylic" and "methacrylic".

Copolymers according to the invention can comprise several kinds of monomer units (i), e.g. carboxylic acid esters with different carboxylic acids and/or different alkoxylate residues. According to a particular embodiment, the monomer units (i) present in the copolymer derive from one carboxylic acid and in particular one of the carboxylic acids described herein as preferred. Copolymers with monomer units (i) essentially composed of monomer units of (meth)acrylic acid esters and in particular methacrylic acid esters are particularly suitable.

Accordingly, the copolymers include in particular monomer units (i) of the formula (IIIa) and/or of the formula (IIIb)

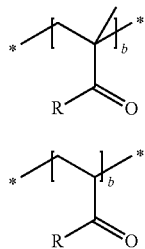

in which
R is one of the alkoxylate residues described herein; and
b can be the same or different and is the mean number of the monomer units of the formula (IIIa) or (IIIb) in the copolymer and corresponds preferably to a number ranging from 1 to 100, advantageously ranging from 5 to 50 and in particular ranging from 11 to 25.

In formula (IIIa) or (IIIb), R is advantageously an alkoxylate residue of the formula (II) and in particular of the formula (IIa).

In principle, all copolymerizable, ethylenically unsaturated comonomers with at least one double bond, in particular monoethylenically unsaturated comonomers, are suitable as monomer units (ii).

Particularly preferred as component (ii) are comonomers of the general formula (IV):

in which
Y is chosen from —OM, —OR$^7$, NH$_2$, —NHR$^7$ or N(R$^7$)$_2$, in which the R$^7$ residues can be identical or different and are chosen from hydrogen, linear or branched C$_1$-C$_{40}$-alkyl, N,N-dimethylaminoethyl, 2-hydroxyethyl, 2-methoxyethyl, 2-ethoxyethyl, hydroxypropyl, methoxypropyl and ethoxypropyl;
M is a cation selected from alkali metal, alkaline earth metal and transition metal cations, in particular Na$^+$, K$^+$, Mg$^{++}$, Ca$^{-+}$ and Zn$^{++}$, NH$_4^+$ and quaternary ammonium cations, in particular alkylammonium, dialkylammonium, trialkylammonium and tetraalkylammonium; and
R$^5$, R$^6$ independently of one another, are chosen from hydrogen, linear or branched C$_1$-C$_8$-alkyl, methoxy, ethoxy, 2-hydroxyethoxy, 2-methoxyethoxy and 2-ethoxyethyl.

Preference is given to the salts, esters and amides of acrylic acid or methacrylic acid, with R$^7$ being selected from hydrogen and linear or branched C$_1$-C$_6$-alkyl, preferably C$_1$-C$_4$-alkyl, and in particular methyl.

Furthermore, allyl esters of linear C$_1$-C$_{40}$, branched C$_3$-C$_{40}$ or carbocyclic C$_3$-C$_{40}$ carboxylic acids, vinyl halides or allyl halides, preferably vinyl chloride and allyl chloride, vinylformamide, vinylmethylacetamide, vinylamine; vinyl- or allyl-substituted heterocyclic compounds, preferably vinylpyridine, vinyloxazoline and allylpyridine, are also suitable.

Comonomers which can likewise be used as monomer units (ii) are olefins, i.e. in principle all unsaturated hydrocarbons with at least one ethylenically unsaturated polymerizable double bond. Olefins with a terminal double bond are advantageous. Monoethylenically unsaturated olefins are preferred. Monoethylenically unsaturated olefins with a terminal double bond are particularly preferred.

Preferred olefins have 4 to 40, in particular 4 and preferably 8 to 24 carbon atoms. According to a particular embodiment, the olefins have 8 or 18 or 20 to 24 carbon atoms.

Suitable olefins include, for example, but-1-ene, but-2-ene, butadiene, 2-methylprop-1-ene (isobutene), pent-1-ene, isoprene, 2-methylbut-1-ene, 3-methylbut-1-ene, hex-1-ene, cyclohexadiene, 2-methylpent-1-ene, 3-methylpent-1-ene, 4-methylpent-1-ene, 2-ethylbut-1-ene, 4,4-dimethylbut-1-ene, 2,4-dimethylbut-1-ene, 2,3-dimethylpent-1-ene, 3,3-dimethylpent-1-ene, 2,4-dimethylpent-1-ene, 3,4-dimethylpent-1-ene, 4,4-dimethylpent-1-ene, oct-1-ene, 2,4,4-trimethylpent-1-ene, 2,4,4-trimethylpent-2-ene, diisobutene, in particular one which exists technically as an isomeric mixture of essentially 2,4,4-trimethylpent-1-ene and 2,4,4-trimethylpent-2-ene, e.g. in a ratio of approx. 80 weight % to approx. 20 weight %, 4,4-dimethylhex-1-ene, 2-ethylhex-1-ene, oligo- and polyisobutenes with a molecular weight of less than 2 000, oligopropenes with a molecular weight of less than 1 000, dec-1-ene, dodec-1-ene, tetradec-1-ene, hexadec-1-ene, heptadec-1-ene, octadec-1-ene, C$_{18}$-1-olefin, C$_{20}$-1-olefin, C$_{22}$-1-olefin, C$_{24}$-1-olefin, C$_{20}$— to C$_{24}$-1-olefin, C$_{24}$- to C$_{28}$-1-olefin, C$_{30}$-1-olefin, C$_{35}$-1-olefin, styrene, alkyl-substituted styrenes, such as a-methylstyrene, tert-butylstyrene or vinyltoluene, cyclic olefins, such as cyclooctene, and mixtures of these monomers.

Ethylene, propylene and vinylidene chloride are also suitable in principle as comonomers for the monomer units (ii).

Additional suitable monomer units (ii) are vinyl ethers, the alcohol part of which has 1 to 30 and preferably 1 to 20 carbon atoms. Mention may in particular be made here of C$_1$-C$_{30}$-alkyl vinyl ethers in which the alkyl residues can be linear, branched or cyclic and substituted or unsubstituted. Examples of suitable alkyl vinyl ethers are methyl vinyl ether, ethyl vinyl ether, propyl vinyl ether, isopropyl vinyl ether, butyl vinyl ether and dodecyl vinyl ether.

Further suitable monomer units (ii) are N-vinylamides. These include in particular non-cyclic representatives, such as N-vinylformamide and N-vinylacetamide, as well as N-vinyllactam. N-Vinyllactams according to the invention are cyclic amides, of which those with 4 to 6 carbon atoms are particularly important. These N-vinyllactams can also exhibit 1, 2 or 3 identical or different alkyl residues with preferably 1 to 4 carbon atoms on the ring. The N-vinyllactams include in particular N-vinylpyrrolidone, N-vinylcaprolactam or the corresponding N-vinyllactams substituted with a methyl or ethyl group.

Comonomers for the monomer units (ii) which may in particular be mentioned are:
methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl(meth)acrylate, 2,3-dihydroxypropyl acrylate, 2,3-dihydroxypropyl methacrylate, 2-hydroxyethyl acrylate, hydroxypropyl acrylate, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylate, glyceryl monoacrylate, glyceryl monomethacrylate and unsaturated sulfonic acids, such as, for example, acrylamidopropanesulfonic acid;
acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth)acrylate, N,N-diethylaminomethyl (meth)acrylate, N,N-dimethylaminoethyl (meth)acrylate, N,N-diethylaminoethyl(meth)acrylate, N,N-dimethylaminobutyl (meth)acrylate, N,N-diethylaminobutyl(meth)acrylate, N,N-dimethylaminohexyl (meth)acrylate, N,N-dimethylaminooctyl(meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl] methacrylamide, N-[3-(diethylamino)propyl] methacrylamide, N-[3-(diethylamino)propyl]acrylamide; diallyldimethylammonium chloride, vinylformamide, vinylmethylacetamide, vinylamine; methyl vinyl ketone, vinylpyridine, vinylimidazole, vinylfuran, styrene, styrenesulfonate, allyl alcohol, and mixtures thereof.

Particularly preferred among these are methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylate, 2-hydroxyethyl methacrylate, hydroxypropyl methacrylate, styrene, unsaturated sulfonic acids, such as, for example, acrylamidopropanesulfonic acid, vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide; 3-methyl-1-vinylimidazolium chloride, 3-methyl-1-vinylimidazolium methyl sulfate, N,N-dimethylaminoethyl methacrylate, N-[3-(dimethylamino)propyl]methacrylamide quaternized with methyl chloride, methyl sulfate or diethyl sulfate.

Comonomers or corresponding monomer units with a basic nitrogen atom can be quaternized.

The basic comonomers can also be cationized by being neutralized with inorganic acids, such as, e.g., sulfuric acid, hydrochloric acid, hydrobromic acid, hydriodic acid, phosphoric acid or nitric acid, or with organic acids, such as, e.g., formic acid, acetic acid, lactic acid or citric acid.

According to a particular embodiment, the copolymers comprise monomer units of at least one ester of acrylic and/or methacrylic acid, wherein the carboxylic acid esters have alkoxylate residues of the general formula (II) or (IIa), as defined herein, and monomer units of an acrylate and/or methacrylate, especially methyl acrylate and methyl methacrylate, as defined herein.

According to one embodiment, copolymers according to the invention comprise one kind of monomer unit (ii), e.g. a monomer unit selected from the group of salts and esters of acrylic acid or methacrylic acid. According to an additional embodiment, copolymers according to the invention comprise two or more kinds of monomer units (ii), e.g. two or more kinds of monomer units selected from the group of salts and esters of acrylic acid or methacrylic acid, or one kind of monomer unit selected from the group of salts and esters of acrylic acid or methacrylic acid and at least one further kind of monomer unit selected from the other copolymerizable monomer units disclosed above.

According to a particular embodiment, the proportion of monomer units (i) preferably amounts to 10 mol % to 99 mol %, advantageously 40 mol % to 95 mol % and in particular 60 mol % to 90 mol % and the proportion of monomer units (ii) preferably amounts to 90 mol % to 1 mol %, advantageously 60 mol % to 5 mol % and in particular 40 mol % to 10 mol %.

In this connection, the fact should be borne in mind that, at relatively low molecular weights, a deviation from the given values can occur due to an increase in the number of specific end monomer units.

The weight-average molecular weight of the copolymerizates according to the invention lies between 5 000 and 800 000 g/mol, preferably between 7 500 and 600 000 g/mol, particularly preferably between 10 000 and 400 000 g/mol.

The copolymers according to the invention are preferably not crosslinked.

The copolymers can be prepared by copolymerization of suitable monomers corresponding to the monomer units (i) and (ii). To this end, the monomers or comonomers can be polymerized using free-radical initiators or else by the action of high-energy radiation, which should be understood as also including the action of high-energy electrons (cf., e.g., EP 9 169 A1, EP 9 170 A1 and EP 276 464).

The polymerization can be carried out, for example, as solution polymerization, bulk polymerization, emulsion polymerization, inverse emulsion polymerization, suspension polymerization, inverse suspension polymerization or precipitation polymerization, without the methods which can be used being limited thereto.

In bulk polymerization, it is possible to proceed such that the monomers of the group (i) and the monomers of the group (ii) are mixed with one another and, after addition of a polymerization initiator, the mixture is fully polymerized. The polymerization can also be carried out semibatchwise by first introducing a portion, e.g. 10%, of the mixture of monomers or comonomers of the groups (i) and (ii) to be polymerized and initiator, by heating the mixture to polymerization temperature and, after the polymerization has started, by adding the remainder of the mixture to be polymerized according to the progress of the polymerization. The copolymerizates can also be obtained by introducing the monomers of the group (i) into a reactor, heating to polymerization temperature, adding at least one monomer of the group (ii) and polymerization initiator, either all at once, stepwise or, preferably, continuously, and polymerizing. The polymerization can in the process be carried out with the assistance of protective colloids, as described in the art.

If desired, the above described polymerization can also be carried out in a solvent. Suitable solvents are, for example, alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, glycerol and dioxane. It is preferred to use solvents which are inert with respect to the carboxylic acid esters used.

The polymerization can also be carried out in water as solvent. In this case, a mixture is first present which is more or less soluble in water depending on the amount of the monomers of the groups (i) and (ii) added. In order to dissolve water-insoluble products which may be formed during the polymerization, it is possible to add, for example, organic solvents such as monohydric alcohols with 1 to 3 carbon atoms, acetone or dimethylformamide. However, it is also possible in the polymerization in water to proceed in such a way that the water-insoluble polymerizates are converted to a finely divided dispersion by addition of conventional emulsifiers or protective colloids, e.g. polyvinyl alcohol.

Examples of emulsifiers which are used are ionic or nonionic surfactants with HLBs ranging from 3 to 13. Reference is made to the publication by W. C. Griffin, J. Soc. Cosmetic Chem., Volume 5, 249 (1954), for the definition of the HLB.

The amount of surfactants, based on the polymerizate, generally amounts to 0.1 to 10 weight %. When water is used as solvent, solutions or dispersions of the polymerizates are obtained. If solutions of the polymerizate in an organic solvent or in mixtures of an organic solvent and water are prepared, 5 to 2 000, preferably 10 to 500, parts by weight of the organic solvent or of the solvent mixture are generally used per 100 parts by weight of the polymerizate.

The copolymers which can be used according to the invention can be obtained in particular by copolymerization (1) of at least one ethylenically unsaturated carboxylic acid and/or of at least one ethylenically unsaturated carboxylic acid derivative, in particular a carboxylic acid ester, and
(2) of at least one additional copolymerizable comonomer, and, if required, partial or complete solvolysis and/or derivatization, in particular esterification or transesterification, of the carboxylic acids and/or carboxylic acid derivatives.

In particular, a copolymer CP' resulting from the copolymerization can, if necessary, be subjected to one or more of the following additional process steps:

(4) an at least partial solvolysis of derivatized carboxylic acid groups;
(5) an esterification of carboxylic acid groups;
(6) an at least partial neutralization of carboxylic acid groups.

The relative amounts of monomers and comonomers to be chosen for the purpose of the copolymerization can be inferred from the above remarks on the proportions of monomer units (i) and (ii).

The polymerization of monomers and comonomers which leads directly to the desired copolymer CP is preferred according to the invention.

The kind of monomers or comonomers to be used does not, though, depend only on the monomer units to be formed. Rather, it is in many cases advisable to polymerize monomers or comonomers which, subsequent to the polymerization reaction, are converted to the desired monomer units. This course of procedure may be conditioned by the reaction and process technology.

In particular, the monomers which can be used for the monomer units (i) can differ from the monomer units involved in the formation of the copolymer CP. Thus, carboxylic acids or specific carboxylic acid derivatives can be polymerized first. The monomer units (i') thus formed, of the copolymer CP', are subsequently as a rule subjected to one or more of the process steps (4), (5) and/or (6), finally resulting in the copolymer CP or a salt thereof. In this sense, it is also possible to polymerize carboxylic acid esters with short-chain, readily hydrolyzable ester groups, such as alkyl esters with preferably 1 to 3 carbon atoms in the alkyl part, their alcohol part subsequently being split off and replaced with another alcohol.

The copolymer CP' obtainable by copolymerization can accordingly comprise carboxyl groups and/or derivatized carboxyl groups, e.g. ester groups, which are subsequently, if desired, converted in a polymer-analogous reaction, generally with formation of the carboxylic acid esters. Preferred polymer-analogous reactions are (4) solvolyses, such as hydrolyses and alcoholyses, of carboxylic acid derivatives, and (5) esterifications of carboxyl groups.

According to one embodiment, copolymers CP to be used according to the invention can be obtained by (i) choosing at least one ethylenically unsaturated carboxylic acid and copolymerizing it with the usual monomers or comonomers, and by reacting at least a portion of the carboxyl groups of the resulting copolymerization product CP' with suitable alcohols with formation of esters.

The polymer-analogous reaction subsequent to the polymerization can be carried out in the presence of a solvent, for example acetone or tetrahydrofuran. However, it is preferable for the copolymer CP' to be reacted directly with the derivatizing agent, e.g. an alcohol corresponding to the abovementioned formula (II). The amount of reactants to be employed depends on the degree of derivatization to be achieved.

If the derivatization is an esterification reaction, this is carried out in the usual way, viz. generally at elevated temperature, e.g. 50 to 200° C. and preferably at 80 to 150° C., if appropriate in the presence of a conventional catalyst, e.g. p-toluenesulfonic acid. Normal reaction times range from 0.5 to 20 and in particular 1 to 10 hours. The reaction of anhydride groups present in the polymer is preferred. This can be carried out, if appropriate, without solvent or in a solvent. If a solvent is used, those organic fluids which are inert to anhydride groups and which dissolve or swell not only the starting material but also the reaction product, viz. the at least partially esterified copolymer, are particularly suitable. Mention may be made in this connection of toluene, xylene, ethylbenzene, aliphatic hydrocarbons and ketones, such as acetone or methyl ethyl ketone. After the esterification, the solvent, if present, is removed from the reaction mixture, for example by distillation.

In order to form salts, the polymerizates can, before or after polymerization, be partially or completely neutralized with bases in order thus, for example, to adjust the water solubility or water dispersibility to a desired extent.

Use may be made, as neutralizing agents for acid groups, of, for example, inorganic bases, such as sodium carbonate, alkali metal hydroxides, such as sodium hydroxide or potassium hydroxide, alkaline earth metal hydroxides and ammonia, or organic bases, such as alkylamines, dialkylamines, trialkylamines, aminoalcohols, especially isopropylamine, ethylamine, diisopropylamine, diethylamine, triisopropylamine, triethylamine, 2-amino-2-methyl-1-propanol, monoethanolamine, diethanolamine, triethanolamine, triisopropanolamine, tri(2-hydroxy-1-propyl)amine, 2-amino-2-methyl-1,3-propanediol or 2-amino-2-hydroxymethyl-1,3-propanediol, and diamines, such as, for example, lysine.

According to a particular embodiment, the seed treatment composition comprises at least 0.1% by weight, preferably at least 0.2% by weight, and in particular at least 1% by weight of the copolymer.

According to a further particular embodiment, the seed treatment composition comprises at most 20% by weight, preferably at most 10% by weight, and in particular at most 3% by weight of the copolymer.

According to one aspect, the weight ratio of the copolymer to solid active ingredient(s) 0.01:1, preferably at least 0.05:1, and in particular at least 0.1:1.

According to another aspect, the weight ratio of the copolymer to the solid ingredient(s) is at most 4:1, preferably at most 1:1, and in particular at most 0.5:1.

Further, the weight ratio of polyarylphenol polyalkoxy ether phosphate and/or polyarylphenol polyalkoxy ether sulfate to copolymer is usually at least 0.1:1, preferably at least 0.2:1, and in particular at least 0.5:1.

On the other hand, the weight ratio of polyarylphenol polyalkoxy ether phosphate and/or polyarylphenol polyalkoxy ether sulfate to copolymer is usually at most 10:1, preferably at most 5:1, and in particular at most 2:1.

In the compositions of the present invention, the polyarylphenol polyalkoxy ether phosphate and/or sulfate and the copolymer having polyalkoxy ether side chains are used as dispersant, especially to provide a dispersion of suspended active ingredient(s).

The present invention thus also relates to the use of a polyarylphenol polyalkoxy ether phosphate and/or sulfate in combination with a copolymer having polyalkoxy ether side chains as dispersant in seed treatment compositions. The polyarylphenol polyalkoxy ether phosphate and/or sulfate are as defined herein. Also, the copolymer having polyalkoxy ether side chains is as defined herein.

The composition of the invention is a seed treatment composition. A seed treatment composition according to the present invention comprises at least one auxiliary agent that is specifically suited for the seed treatment, i.e. an auxiliary agent which in particular promotes adhesion of the active ingredient to and/or penetration into the seeds and/or otherwise improves stability and/or manageability of the composition or the seeds treated therewith. Thus, the seed treatment composition the present invention comprises at least one seed treatment auxiliary agent(s), and optionally one or more further auxiliary agents.

In particular, seed treatment auxiliary agents are selected from the group consisting of agents suitable for seed coating materials, agents suitable for solid matrix priming materials, penetration enhancers suitable for promoting seed imbibition, colorants, antifreezes, and gelling agents.

According to a preferred embodiment, the seed coating material comprises a binder (or sticker). Optionally, the coating material also comprises one or more additional seed treatment auxiliary agents selected from the group consisting of fillers and plasticizers.

Binders (or stickers) are all customary binders (or stickers) which can be employed in seed treatment compositions. Binders (or stickers) that are useful in the present invention preferably comprise an adhesive polymer that may be natural or partly or wholly synthetic and is without phytotoxic effect on the seed to be coated. Preferably, the binder (or sticker) is biodegradable.

The binder (or sticker) may be selected from polyesters, polyether esters, polyanhydrides, polyester urethanes, polyester amides; polyvinyl acetates; polyvinyl acetate copolymers; polyvinyl alcohols and tylose; polyvinyl alcohol copolymers; polyvinylpyrolidones; polysaccharides, including starches, modified starches and starch derivatives, dextrins, maltodextrins, alginates, chitosans and celluloses, cellulose esters, cellulose ethers and cellulose ether esters including ethylcelluloses, methylcelluloses, hydroxymethylcelluloses, hydroxypropylcelluloses and carboxymethylcellulose; fats; oils; proteins, including casein, gelatin and zeins; gum arabics; shellacs; vinylidene chloride and vinylidene chloride copolymers; lignosulfonates, in particular calcium lignosulfonates; polyacrylates, polymethacrylates and acrylic copolymers; polyvinylacryhates; polyethylene oxide; polybutenes, polyisobutenes, polystyrene, polyethyleneamines, polyethylenamides; acrylamide polymers and copolymers; polyhydroxyethyl acrylate, methylacrylamide monomers; and polychloroprene.

In a particular embodiment of the invention the seed treatment composition contains at least one polyester, which, in particular, is selected from polylactides, partially aromatic polyesters (copolymers of terephthalic acid, adipic acid and aliphatic diols), polyglycolides, polyhydroxyalkanoates and polytartrates.

The amount of binder (or sticker) in the composition can vary, but, if present, will be in the range of about 0.01 to about 25% of the total weight, more preferably from about 1 to about 15%, and even more preferably from about 5% to about 10%.

As mentioned above, the coating material can optionally also comprise a filler. The filler can be an absorbent or an inert filler, such as are known in the art, and may include wood flours, cereal flours, tree bark mill, wood meal and nut shell meal, sugars, in particular polysaccharides, activated carbon, fine-grain inorganic solids, silica gels, silicates, clays, chalk, diatomaceous earth, calcium carbonate, magnesium carbonate, dolomite, magnesium oxide, calcium sulfate and the like. Clays and inorganic solids which may be used include calcium bentonite, kaolin, china clay, talc, perlite, mica, vermiculite, silicates, quartz powder, montmorillonite, attapulgite, bole, loess, limestone, lime and mixtures thereof. Sugars which may be useful include dextrin and maltodextrin. Cereal flours include wheat flour, oat flour and barley flour. The filler may also comprise fertilizer substances such as, for example, ammonium sulfate, ammonium phosphate, ammonium nitrate, ureas and mixtures thereof.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components, if present, will be in the range of about 0.05 to about 75% of the total weight, more preferably about 0.1 to about 50%, and even more preferably about 0.5% to 15%.

It is preferred that the binder (or sticker) be selected so that it can serve as a matrix for the active ingredient(s). While the binders disclosed above may all be useful as a matrix, it is preferred that a continuous solid phase of one or more binder compounds is formed throughout which is distributed as a discontinuous phase the active ingredient(s). Optionally, a filler and/or other components can also be present in the matrix. The term "matrix" is to be understood to include what may be viewed as a matrix system, a reservoir system or a microencapsulated system. In general, a matrix system consists of the active ingredient(s) and a filler uniformly dispersed within a polymer, while a reservoir system consists of a separate phase comprising the active ingredient(s) that is physically dispersed within a surrounding, rate-limiting, polymeric phase. Microencapsulation includes the coating of small particles or droplets of liquid, but also to dispersions in a solid matrix.

Especially if the active ingredient(s) used in the coating is an oily type composition and little or no inert filler is present, it may be useful to hasten the drying process by drying the composition. This optional step may be accomplished by means well known in the art and can include the addition of fillers such as calcium carbonate, kaolin or bentonite clay, perlite, diatomaceous earth, or any absorbent material that is added preferably concurrently with the active ingredient(s) coating layer to absorb the oil or excess moisture. The amount of absorbent necessary to effectively provide a dry coating will be in the range of about 0.5 to about 10% of the weight of the seed.

Optionally, the coating material comprises a plasticizer. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used; however, useful plasticizers include polyethylene glycol, oligomeric polyalkylene glycols, glycerol, alkylbenzylphthalates, in particular butylbenzylphthalate, glycol benzoates and related compounds. The range of plasticizer, if present, in the coating layer will be in the range of from about 0.1% by weight to about 20% by weight.

Agents suitable for solid matrix priming materials which are useful in the present invention include polyacrylamide, starch, clay, silica, alumina, soil, sand, polyurea, polyacrylate, or any other material capable of absorbing or adsorbing the active ingredient(s) and releasing the active ingredient(s) into or onto the seed. It is useful to make sure that active ingredient(s) and the solid matrix material are compatible with each other. For example, the solid matrix material should be chosen so that it can release the active ingredient(s) at a reasonable rate, for example over a period of minutes, hours, or days.

Penetration enhancers suitable for promoting seed imbibition include agriculturally acceptable surface active compounds. The amount of penetration enhancers will usually not exceed 20% by weight, based on the total weight of the composition. Preferably, the amount of penetration enhancers, if present, will be in the range from 2% to 20% by weight.

Colorants according to the invention are all dyes and pigments which are customary for such purposes. In this context, both pigments, which are sparingly soluble in water, and dyes, which are soluble in water, may be used. Examples which may be mentioned are the colorants, dyes and pigments known under the names Rhodamin B, C. I. Pigment Red 112 and C. I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 108. The amount of colorants, if present, will usually not exceed 20% by weight of the composition and preferably ranges from 1 to 15% by weight, based on the total weight of the composition. It is generally preferred if the colorants are also active as repellents for warm-blooded animals, e.g. iron oxide, $TiO_2$, Prussian blue, anthraquinone dyes, azo dyes and metal phthalocyanine dyes.

Antifreezes which can be employed especially for aqueous compositions are in principle all those substances which lead to a depression of the melting point of water. Suitable antifreezes comprise alcohols such as methanol, ethanol, isopropanol, butanols, glycol, glycerine, diethyleneglycol and the like. Typically, the amount of antifreeze will not exceed 20% by weight and, if present, frequently ranges from 1 to 15% by weight, based on the total weight of the composition.

Gelling agents which are suitable are all substances which can be employed for such purposes in agrochemical compositions, for example cellulose derivatives, polyacrylic acid derivatives, xanthan, modified clays, in particular organically modified phyllosilicates and highly-dispersed silicates. A particularly suitable gelling agent is carrageen (Satiagel®). Usually, the amount of gelling agent will not exceed 5% by weight of the composition and, if present, preferably ranges from 0.5 to 5% by weight, based on the total weight of the composition.

Further auxiliary agents that may be present in the seed treatment composition include solvents, wetters, dispersants, emulsifiers, surfactants, thickeners, protective colloids, antifoams, and preservatives.

Water is a preferred solvent. According to a particular embodiment, the compositions of the present invention comprise at least 5% by weight, preferably at least 10% by weight and in particular at least 30% by weight of water. On the other hand, the compositions of the present invention usually comprise at most 99% by weight, preferably at most 90% by weight and in particular at most 80% by weight of water.

Further examples of suitable solvents are organic solvents such as aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used. However, according to a particular embodiment, the compositions of the present invention contain less than 15% by weight and preferably less than 6% by weight of said organic solvents.

Surface active compounds are all those surfactants which are suitable for formulating agrochemical actives, in particular for active ingredient(s), and which may be nonionic, cationic, anionic or amphoteric. According to their action, surfactants—sometimes referred to as "additives"—may be divided into wetters, dispersants, emulsifiers or protective colloids; however, these particular groups may overlap and cannot be divided strictly.

Because the compositions of the present invention comprise a polyarylphenol polyalkoxy ether phosphate and/or a polyarylphenol polyalkoxy ether sulfate and a copolymer having polyalkoxy ether side chains, usually no further dispersants need to be added to the composition. Typically, the amount of further dispersants will not exceed 10% by weight. Preferably, it does not exceed 5% by weight and in particular 1% by weight, based on the total weight of the composition. According to a particular embodiment, the compositions of the present invention do not contain significant amounts of further dispersants, i.e. they contain no further dispersant or the amount is below 0.5% by weight and preferably below 0.1% by weight, based on the total weight of the composition. Also, the amount of further surfactants having an HLB value of more than will typically not exceed 10% by weight. Preferably, it does not exceed 5% by weight and in particular 1% by weight. According to a particular embodiment, the compositions of the present invention do not contain significant amounts of such further surfactants, i.e. they contain no such further surfactant or the amount is below 0.5% by weight and preferably below 0.1% by weight, based on the total weight of the composition.

Suitable wetters are all those substances which promote wetting and which are conventionally used for formulating agrochemical active ingredients. Alkylnaphthalenesulfonates such as diisopropyl- or diisobutylnaphthalenesulfonates can be used preferably.

Dispersants and/or emulsifiers which are suitable are all nonionic, anionic and cationic dispersants or emulsifiers conventionally used for formulating agrochemical active ingredients. The following can preferably be used: nonionic or anionic dispersants and/or emulsifiers or mixtures of nonionic or anionic dispersants and/or emulsifiers.

Suitable nonionic dispersants and/or emulsifiers which may be employed are, in particular, ethylene oxide/alkylene oxide block copolymers, alkylphenol polyglycol ethers and tristryrylphenol polyglycol ethers, for example polyoxyethylene octylphenol ether, ethoxylated isooctylphenol, octylphenol, nonylphenol, alkylphenol polyglycol ether, tributylphenyl polyglycol ether, tristearylphenyl polyglycol ether, alkylarylpolyether alcohols, alcohol and fatty alcohol ethylene oxide condensates, ethoxylated castor oil, polyoxyethylene alkyl ether, ethoxylated polyoxypropylene, lauryl alcohol polyglycol ether acetal, sorbitol esters and methyl cellulose.

Suitable anionic dispersants and/or emulsifiers which may be employed are, in particular, alkali metal, alkaline earth metal and ammonium salts of ligninsulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore arylsulfonate/formaldehyde condensates, for example condensates of sulfonated naphthalene and naphthalene derivatives with formaldehyde, condensates of naphthalene or of naphthalenesulfonic acid with phenol and formaldehyde, ligninsulfonates, ligninsulfite waste liquors, phosphated or sulfated derivatives of methylcellulose, and salts of polyacrylic acid.

Thickeners are typically water-soluble polymers which exhibit suitable plastic properties in an aqueous medium. Examples include gum arabic, gum karaya, gum tragacanth, guar gum, locust bean gum, xanthan gum, carrageenan, alginate salt, casein, dextran, pectine, agar, 2-hydroxyethyl starch, 2-aminoethyl starch, 2-hydroxyethyl cellulose, methyl cellulose, carboxymethyl cellulose salt, cellulose sulfate salt. Xanthan gum is preferred. Usually, the amount of thickener will not exceed 20% by weight and, if present, frequently ranges from 1 to 15% by weight, based on the total weight of the composition.

Protective colloids are typically water soluble, amphiphilic polymers. Examples include proteins and denatured proteins such as casein, polysaccharides such as water soluble starch derivatives and cellulose derivatives, in particular hydrophobic modified starch and celluloses, furthermore polycarboxylates such as polyacrylic acid and acrylic acid copolymers, polyvinylalcohol, polyvinylpyrrolidone, vinylpyrrolidone copolymers, polyvinyl amines, polyethylene imines and polyalkylene ethers. Usually, the amount of protective colloid will not exceed 3% by weight of the composition and, if present, preferably ranges from 0.1 to 2% by weight, based on the total weight of the composition.

Antifoams which can be employed are all those substances which inhibit the development of foam and which are conventionally used for formulating agrochemical active ingredients. Silicone antifoams, i.e. aqueous silicon emulsions (e.g. Silikon® SRE by Wacker or Rhodorsil® by Rhodia), long chain alcohols, fatty acids and salts thereof, e.g. and magnesium stearate are particularly suitable. Usually, the amount of antifoam will not exceed 3% by weight of the composition and, if present, preferably ranges from 0.1 to 2% by weight, based on the total weight of the composition.

Preservatives which can be employed are all preservatives used for such purposes in agrochemical compositions. Examples which may be mentioned are dichlorophene, isothiazolenes and isothiazolones such as 1,2-benzisothiazol-3(2H)-one, 2-methyl-2H-isothiazol-3-one-hydrochloride, 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one-hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one-calcium chloride complex, 2-octyl-2H-isothiazol-3-one and benzyl alcohol hemiformal. Usually, the amount of preservatives will not exceed 2% by weight of the composition and, if present, preferably ranges from 0.01 to 1% by weight, based on the total weight of the composition.

The skilled person is essentially familiar with agricultural compositions of active ingredients (see, for instance, Ullmann's Encyclopedia of Industrial Chemistry, Fungicides Chapter 4, 5th ed. on CD-ROM, Wiley-VCH, 1997 and Mollet, H., Grubemann, A., Formulation technology, Wiley VCH Verlag GmbH, Weinheim (Federal Republic of Germany), 2001, which is incorporated herein by reference in its entirety). Examples include water-soluble concentrates (SL, LS), dispersible concentrates (DC), emulsifiable concentrates (EC), emulsions (EW, EO, ES), suspensions (SC, OD, FS), water-dispersible granules (WG, SG), water-dispersible or water-soluble powders (WP, SP, SS, WS), dusts or dustable powders (DP, DS), granules (GR, FG, GG, MG), ULV solutions (UL) and gel formualtions (GF). For seed treatment purposes, such compositions may be applied as such or after addition of a suitable liquid, in particular water, in order to dissolve, emulsify, disperse, suspend or dilute the composition. The type of the ready-to-use preparation applied to the seeds thus depends on the type of composition used and the method used for treating the seeds.

The compositions can be prepared in the known manner, for example by extending the active ingredient component with one or more auxiliary agents (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), all of which being incorporated by reference in its entirety).

The following formulations simply illustrate said compositions:

A Dispersible Concentrates (DC)

20 parts by weight of the active ingredient(s) are dissolved in 70 parts by weight of cyclohexanone with addition of 10 parts by weight of dispersant(s), whereby a formulation with 20% (w/w) of the active ingredient(s) is obtained. Dilution with water gives a dispersion.

B Suspensions (SC, OD, FS)

In an agitated ball mill, 20 parts by weight of the active ingredient(s) are comminuted with addition of 10 parts by weight of dispersant(s) and optionally wetter(s) and 70 parts by weight of water or of an organic solvent to give a fine active compound(s) suspension, whereby a formulation with 20% (w/w) of the active ingredient(s) is obtained. Dilution with water gives a stable suspension of the active ingredient(s).

C Water-Dispersible Granules (WG, SG)

50 parts by weight of the active ingredient(s) are ground finely with addition of 50 parts by weight of dispersant(s) and optionally wetter(s) and made as water-dispersible or water-soluble granules by means of technical appliances (for example extrusion, spray tower, fluidized bed), whereby a formulation with 50% (w/w) of the active ingredient(s) is obtained. Dilution with water gives a stable dispersion or solution of the active compound(s).

D Water-Dispersible Powders (WP, WS)

75 parts by weight of the active ingredient(s) are ground in a rotor-stator mill with addition of 25 parts by weight of dispersant(s) and optionally wetter(s), and silica gel, whereby a formulation with 75% (w/w) of the active ingredient(s) is obtained. Dilution with water gives a stable dispersion or solution of the active ingredient(s).

E Gel Formulation (GF)

In an agitated ball mill, 20 parts by weight of the active ingredient(s) are comminuted with addition of 10 parts by weight of dispersant(s), 1 part by weight of a gelling agent and 70 parts by weight of water or of an organic solvent to give a fine active compound(s) suspension, whereby a formulation with 20% (w/w) of the active ingredient(s) is obtained. Dilution with water gives a stable suspension of the active ingredient(s).

Formulations A-E can be diluted with water before application or directly applied.

According to a particular embodiment of present invention, the seed treatment composition is a liquid or is applied as a liquid. Preference is given to a suspension and especially an aqueous suspension. The suspended particles are active ingredient(s) or auxiliary agents having a melting point above 30° C.

For the seed treatment according to the present invention, powders or granules, such as water-dispersible powders or granules, and suspensions are preferred. Further, gel formulations are preferred.

According to the present invention, the following formulations are particularly preferred: flowable concentrates (especially FS). Also preferred are gel formulations (especially GF). These formulations can be applied to the seed diluted or undiluted.

According to a particular embodiment, the invention relates to a FS formulation. Typically, an FS formulation may comprise 1-800 g/l of the active ingredient(s), 1-200 g/l polyarylphenol polyalkoxy ether sulfate and/or phosphate, 1-200 g/l of a copolymer having polyalkoxy ether side chains, 0 to 200 g/l antifreezing agent, 0 to 400 g/l of binder, 0 to 200 g/l of a colorant and up to 1 liter of a solvent, preferably water.

According to a further particular embodiment, the seed treatment composition of the present invention is a seed coating formulation.

Such seed coating formulations comprise the active ingredient(s), the dispersants and at least one binder (or sticker) and optionally at least one further auxiliary agent that is selected from the group consisting of fillers and plasticizers.

Seed coating formulations comprising binders, fillers and/or plasticizers are well-known in the art. Seed coating formulations are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

The amount of the active ingredient(s) that is included in the coating formulation will vary depending upon the type of seed, but the coating formulation will contain an amount of the active ingredient(s) that is pesticidally effective. In general, the amount of the active ingredient(s) in the coating formulation will range from about 0.005 to about 75% of the total weight. A more preferred range for the active ingredient(s) is from about 0.01 to about 40%; more preferred is from about 0.05 to about 20%.

The exact amount of the active ingredient(s) that is included in the coating formulation is easily determined by one skilled in the art and will vary depending upon the size and other characteristics (surface structure etc.) of the seed to be coated. The active ingredient(s) of the coating formulation must not inhibit germination of the seed and should be efficacious in protecting the seed and/or the plant during that time in the target pest's life cycle in which it causes injury to the seed or plant. In general, the coating will be efficacious for approximately 0 to 120 days, preferably for approximately 0 to 60 days, after sowing.

The coating formulations formed with the active ingredient(s) are capable of effecting a slow rate of release of the active ingredient(s) by diffusion or movement through the matrix into the seed or to the surrounding medium.

The present invention also relates to the use of a composition as defined herein for treating seed.

The present invention also relates to a method of treating seed with a composition described herein, which comprises applying an effective amount of a composition as disclosed herein to a lot of seeds.

The term "batch" or "lot" means a group of seeds that are undergoing the seed treatment. The amount and weight of the seeds can vary depending on the treatment.

The term "loading" refers to the actual amount of an active ingredient that is adhered onto each seed, based on bulk amount of seed.

As used herein, the term "seed" denotes any resting stage of a plant that is physically detached from the vegetative stage of a plant and/or may be stored for prolonged periods of time and/or can be used to re-grow another plant individual of the same species. Here, the term "resting" refers to a state wherein the plant retains viability, within reasonable limits, in spite of the absence of light, water and/or nutrients essential for the vegetative (i.e. non-seed) state. In particular, the term refers to true seeds but does not embraces plant propagules such as suckers, corms, bulbs, fruit, tubers, grains, cuttings and cut shoots.

As used herein, the term "plant" means an entire plant or parts thereof. The term "entire plant" refers to a complete plant individual in its vegetative, i.e. non-seed stage, characterized by the presence of an arrangement of roots, shoots and foliage, depending on the developmental stage of the plant also flowers and/or fruits, all of which are physically connected to form an individual which is, under reasonable conditions, viable without the need for artificial measures. The term may also refer to an entire plant harvested as such.

The term "plant parts" refers to roots, shoots, foliage, flowers or other parts of the vegetative stage of the plant, which, when dislodged and disconnected from the rest, are incapable of survival, unless supported by artificial measures or able to re-grow the missing parts to form an entire plant. As used herein, fruits are also considered as plant parts.

As used herein, the term "root" refers to parts of a plant which are normally, in order to fulfill their physiological functions, located beneath the soil surface. Preferably, the term denotes the parts of a plant which are below the seed and have directly emerged from the latter, or from other roots, but not from shoots or foliage.

As used herein, the "shoots and foliage" of a plant are to be understood to be the shoots, stems, branches, leaves and other appendages of the stems and branches of the plant after the seed has sprouted, but not including the roots of the plant. It is preferable that the shoots and foliage of a plant be understood to be those non-root parts of the plant that have grown from the seed and are located a distance of at least one inch away from the seed from which they emerged (outside the region of the seed), and more preferably, to be the non-root parts of the plant that are at or above the surface of the soil.

As used herein, "fruits" are considered to be the parts of a plant which contain seeds and/or serve to spread seeds, and/or which may be removed from a plant without impairing its viability.

According to the present invention, the seed treatment comprises applying a composition of the invention to a seed.

Although the present method can be applied to a seed in any physiological state, it is preferred that the seed be in a sufficiently durable state that it incurs no significant damage during the treatment process. Typically, the seed is a seed that has been harvested from the field; removed from the plant; and/or separated from the fruit and any cob, pod, stalk, outer husk, and surrounding pulp or other non-seed plant material. The seed is preferably also biologically stable to the extent that the treatment would cause no biological damage to the seed. In one embodiment, for example, the treatment can be applied to seed that has been harvested, cleaned and dried to a moisture content below about 15% by weight. In an alternative embodiment, the seed can be one that has been dried and then primed with water and/or another material and then re-dried before or during the treatment with a composition of the invention.

The term seed treatment comprises all suitable seed treatment and especially seed dressing techniques known in the art, such as seed coating (e.g. seed pelleting), seed dusting and seed imbibition (e.g. seed soaking). Here, "seed treatment" refers to all methods that bring seeds and a composition of the invention into contact with each other, and "seed dressing" to methods of seed treatment which provide the seeds with an amount of the active ingredient, i.e. which generate a seed comprising the active ingredient. In principle, the treatment can be applied to the seed at any time from the harvest of the seed to the sowing of the seed. The seed can be treated immediately before, or during, the planting of the seed, for example using the "hopper-box" or "planter-box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

When it is said that unsown seed is "treated", such treatment is not meant to include those practices in which the pesticide is applied to the soil, rather than directly to the seed.

By applying the treatment to the seed prior to the sowing of the seed the operation is simplified. In this manner, seeds can be treated, for example, at a central location and then dispersed for planting. This permits the person who plants the seeds to avoid the handling and use of the active ingredient and to merely handle and plant the treated seeds in a manner that is conventional for regular untreated seeds, which reduces human exposure.

Specifically, the seed treatment follows a procedure in which the seed is exposed to the specifically desired amount of a preparation comprising the active ingredient(s). The preparation may be a composition of the present invention that is applied as such or after previously diluting it, e.g. with water; for instance, it may be expedient to dilute seed treatment compositions 2-10 fold leading to concentrations in the ready-to-use compositions of 0.01 to 60% by weight active compound by weight, preferably 0.1 to 40% by weight. In some instances, it may be expedient to add the dispersants of the present invention to a composition that has no or insufficient amounts of dispersant. Upon addition of the dispersants and optional dilution with water the resulting composition will form a dispersion.

Thus, the active ingredient concentrations in ready-to-use preparation can be varied within substantial ranges. In general, they are in the range from 0.01 and 80% by weight, frequently in the range from 0.1 to 50% by weight, preferably in the range from 0.5 and 20% by weight, based on the total weight of the preparation. The active ingredients can also successfully be used in concentrated form, it being possible to apply, to the seed, preparations with more than 80% by weight of active ingredient, or even the active ingredient without additions. The amount of additives will generally not exceed 30% by weight, preferably 20% by weight, and is, in particular, in the range of from 0.1 to 20% by weight, in each case based on the total weight of the preparation.

Usually, a device which is suitable for seed treatment, for example a mixer for solid or solid/liquid components, is employed until the preparation is distributed uniformly on the seed. Thus, the preparation can be applied to seeds by any standard seed treatment methodology, including but not limited to mixing in a container (e.g., a bottle, bag or tumbler), mechanical application, tumbling, spraying, and immersion. If appropriate, this is followed by drying.

Particular embodiments of the present invention comprise seed coating and imbibition (e.g. soaking). "Coating" denotes any process that endows the outer surfaces of the seeds partially or completely with a layer or layers of non-plant material, and "imbibition" any process that results in penetration of the active ingredient(s) into the germinable parts of the seed and/or its natural sheath, (inner) husk, hull, shell, pod and/or integument. The invention therefore also relates to a treatment of seeds which comprises providing seeds with a coating that comprises the active ingredient(s), and to a treatment of seeds which comprises imbibition of seeds with the active ingredient(s).

Coating is particularly effective in accommodating high loads of the active ingredient(s), as may be required to treat typically refractory pests, while at the same time preventing unacceptable phytotoxicity due to the increased load of the active ingredient(s).

Coating may be applied to the seeds using conventional coating techniques and machines, such as fluidized bed techniques, the roller mill method, rotostatic seed treaters, and drum coaters. Other methods such as the spouted beds technique may also be useful. The seeds may be pre-sized before coating. After coating, the seeds are typically dried and then transferred to a sizing machine for sizing.

Such procedures are known in the art. Seed coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017.

In another particular embodiment, the solid the active ingredient(s), for instance as a solid fine particulate formulation, e.g. a powder or dust, can be mixed directly with seeds. Optionally, a sticking agent can be used to adhere the solid, e.g. the powder, to the seed surface. For example, a quantity of seed can be mixed with a sticking agent (which increases adhesion of the particles on the surface of the seed) and optionally agitated to encourage uniform coating of the seed with the sticking agent. For example, the seed can be mixed with a sufficient amount of sticking agent, which leads to a partial or complete coating of the seed with sticking agent. The seed pretreated in this way is then mixed with a solid formulation containing the active ingredient(s) to achieve adhesion of the solid formulation on the surface of the seed material. The mixture can be agitated, for example by tumbling, to encourage contact of the sticking agent with the active ingredient(s), thereby causing the solid the active ingredient(s) to stick to the seed.

Another particular method of treating seed with the active ingredient(s) is imbibition. For example, seed can be combined for a period of time with an aqueous solution comprising from about 1% by weight to about 75% by weight of the active ingredient(s) in a solvent such as water. Preferably the concentration of the solution is from about 5% by weight to about 50% by weight, more preferably from about 10% by weight to about 25% by weight. During the period that the seed is combined with the solution, the seed takes up (imbibes) at least a portion of the active ingredient(s). Optionally, the mixture of seed and solution can be agitated, for example by shaking, rolling, tumbling, or other means. After the imbibition process, the seed can be separated from the solution and optionally dried in a suitable manner, for example by patting or air-drying.

In yet another particular embodiment of the present invention, the active ingredient(s) can be introduced onto or into a seed by use of solid matrix priming. For example, a quantity of the active ingredient(s) thereof can be mixed with a solid matrix material, and then the seed can be placed into contact with the solid matrix material for a period to allow the active ingredient(s) to be introduced to the seed. The seed can then optionally be separated from the solid matrix material and stored or used, or, preferably, the mixture of solid matrix material plus seed can be stored or planted/sown directly.

In each embodiment of the invention, it is preferred that the composition of the invention is applied to a seed in an effective amount, that is, an amount sufficient to provide sufficient active ingredient, e.g. for protection against pests, to the seed and the plant that grows from the seed. A seed treatment according to the present invention is therefore for protecting not only the seed but also the plant that grows from the seed.

As used herein, "protection" is achieved if the percent of feeding damage to the seed and/or the plant at 10 days after infestation (DAI) with the pest is significantly reduced for treated seeds or plants grown from treated seeds as compared to untreated seeds or plants grown from untreated seeds. In order to be effective, the active ingredient is generally employed in an amount of from 0.1 to 500 g, preferably 0.5 to 200 g, and in particular 0.75 to 100 g, per 100 kilograms of seed.

According to the present invention one purpose of said seed treatment is to control a pest. Such a seed treatment thus involves a pesticidal effect or a pesticidal activity providing protection against damage done by the pest to a seed and/or a plant grown from the seed. Seed treatment can especially be used to protect seeds and seedlings from early season disease and insect pests affecting crop emergence and growth.

As used herein, the terms "pesticidal effect" and "pesticidal activity" mean any direct or indirect action on the target pest that results in reduction of feeding damage on the treated seeds as well as on the fruits, roots, shoots and/or foliage of plants grown from treated seeds as compared untreated seeds or to plants grown from untreated seeds, respectively. The terms "active against a (first or second) pest" also have the same meaning. Such direct or indirect actions include killing of the pest, repelling the pest from the plant seeds, fruits, roots, shoots and/or foliage, inhibiting feeding of the pest on, or the laying of its eggs on, the plant seeds, fruits, roots, shoots and/or foliage, and inhibiting or preventing reproduction of the pest.

Pests in particular include soil-borne and soil-dwelling, shoot and foliage pests.

Particular fungi to be controlled include the following: *Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.) on corn (e.g. *D. maydis*), cereals (e.g. *B. sorokiniana*: spot blotch), rice (e.g. *B. oryzae*) and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn, rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassficola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (takeall) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphani-dermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (Septoria blotch) on wheat and *S.* (syn. *Stagonospora*) *nodorum* (Stagonospora blotch) on cereals; *Uncinula* (syn. *Erysiphe*) *necator* (powdery mildew, anamorph: *Oidium tuckeri*) on vines; *Setosphaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

Particular insects to be controlled include the following:

lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorhynchus assimilis, Ceuthorhynchus napi, Chaetocnema tibialis, Conoderus vespertinus, Crioceris asparagi, Ctenicera* ssp., *Diabrotica longicomis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brun-* neipennis, *Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freebomi, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci;* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichtysi, Brachycaudus persicae, Brachycaudus prunicola, Brevicoryne brassicae, Capitophorus homi, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantii-* and, *Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria anguilfera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis; Araneida,* e.g. *Latrodectus mactans,* and *Loxosceles reclusa;* fleas (Siphonaptera), e.g. *Ctenocephalides fells, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica*,
centipedes (Chilopoda), e.g. *Scutigera coleoptrata*,
millipedes (Diplopoda), e.g. *Narceus* spp.,
Earwigs (Dermaptera), e.g. *forficula auricularia*,
lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.
Collembola (springtails), e.g. *Onychiurus* ssp.

The compositions of the present invention are also suitable for controlling Nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compositions of the present invention are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri*, and *oligonychus pratensis*.

The present invention also provides a seed that has been treated by the method described herein. It also provides a seed obtainable by the method described herein.

Further, the present invention also provides a seed that has been treated with the seed treatment composition described herein, and in particular that is coated with the composition or contains it. It also provides a seed obtainable by using the composition described herein.

According to a particular embodiment, the seeds treated with the composition of the present invention have a loading of active ingredient(s) of 0.1 to 500 g, preferably 0.5 to 200 g, and in particular 0.75 to 100 g, per 100 kilograms of seed.

The term "coated with and/or contains" here signifies that the active ingredient(s) is for the most part on the surface of the seed at the time of application, although a greater or lesser part of the active ingredient(s) may penetrate into the seed, depending on the method of application. When the said seed is (re)planted, it may absorb the active ingredient(s).

According to one embodiment, such a seed comprising the active ingredient(s) has a coating, wherein the coating comprises the active ingredient(s). According to a further embodiment, such a seed comprising the active ingredient(s) is a seed whose germinable part and/or natural sheath, shell, pod and/or integument comprise(s) the active ingredient(s). Also, the active ingredient(s) can be present in both the coating and the germinable part and/or natural sheath, shell, pod and/or integument of the seed.

Preferably, such seeds comprise an effective amount of the active ingredient(s). Accordingly, the seeds are coated, impregnated or coated and impregnated in such a manner that pest damage during germination and emergence is reduced.

The seeds treated with the composition of the present invention may also be enveloped with a film overcoating to protect the coating containing the active ingredient(s). Such overcoatings are known in the art and may be applied using conventional fluidized bed and drum film coating techniques.

The seeds of the present invention can be used for the propagation of plants. The seeds can be stored, handled, planted/sowed and tilled.

EXAMPLES

The invention will be illustrated by the following examples, which should not be construed as limiting the invention.

Example 1 to 7

Suspension concentrates were produced by mixing all ingredients (except xanthan gum) and milling these suspensions in two steps, first on a mechanical mill and then in a bead mill to a particle size characterised by having $D_{90}<6$ μm as determined by laserdiffraction. Finally, the xanthan gum was added in the form of a 2%-solution in water.

|  | 1 | 2 | 2a | 3 | 3a | 4 | 5 | 6 | 7 |
|---|---|---|---|---|---|---|---|---|---|
| epoxiconazole | 200 | — | — | — | — |  | — | — | — |
| alpha-cypermethrin | — | 500 | 500 | — | — | — | — | — | — |
| triticonazole | — | — | — | 200 | 200 | 25 |  |  |  |
| pigment red 48:2 |  |  |  |  |  | 45 |  |  |  |

-continued

| | 1 | 2 | 2a | 3 | 3a | 4 | 5 | 6 | 7 |
|---|---|---|---|---|---|---|---|---|---|
| pyraclostrobin | — | — | — | — | — | — | 200 | — | — |
| fipronil | — | — | — | — | — | — | — | 600 | — |
| fluquinconazole | — | — | — | — | — | — | — | — | 100 |
| PE10500 | — | — | — | — | 20 | — | — | — | — |
| Soprophor 4D384 | 10 | 20 | 40 | 10 | | 20 | 10 | 5 | 10 |
| Atlox 4913 | 33 | 66.7 | | 33 | | 30 | 30 | 15 | 30 |
| glycerol | 100 | 60 | 60 | 100 | 100 | 138 | 100 | 60 | 150 |
| xanthan gum 2% in water | 130 | 60 | 60 | 100 | 100 | 130 | 150 | 40 | 40 |
| water | 610 | 400 | 447 | 630 | 650 | 670 | 550 | 470 | 640 |
| D90 fresh [µm] | 3.6 | 3.5 | 3.2 | 2.5 | 2.2 | 3.2 | 4.0 | 2.2 | 3.3 |
| D90 after 2W50 [µm] | 3.6 | 4.8 | 6.1 | 3.3 | 4.2 | — | — | — | — |
| D90 after 8W40 [µm] | — | — | — | — | — | 3.3 | 4.8 | 2.4 | 3.4 |
| Serum [%] | 6 | — | 9 | 21 | 49 | 2 | 13 | 6.5 | 10.4 |

The formulations according to examples 1 to 7 illustrate the compositions of the invention. The formulations of examples 2a and 3a are for comparative purposes.

We claim:

1. A method of treating seed, which comprises applying to a lot of seeds an effective amount of a composition comprising an active ingredient;

a polyarylphenol polyalkoxy ether phosphate and/or polyarylphenol polyalkoxy ether sulfate having the formula (I):

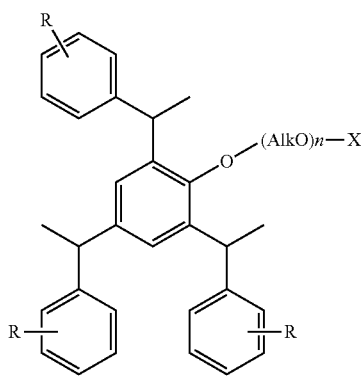

wherein each R independently represents hydrogen or $C_1$-$C_4$ alkyl; Alk represents $C_2$-$C_6$ alkylene; n has a value from 5 to 60; and X is —$SO_3H_2$ or —$PO_3H$; or an agriculturally acceptable base addition salt thereof; and a copolymer comprising:
  (i) monomer units of at least one ester of an ethylenically unsaturated carboxylic acid, wherein the carboxylic acid ester has an alkoxylate residue of the general formula (II):

in which
  $R^1$ is hydrogen or an aliphatic hydrocarbon residue with 1 to 40 carbon atoms;
  $R^2$, $R^3$, $R^4$ are, independently of one another, hydrogen or $C_1$-$C_4$- alkyl;

w, x, z correspond, independently of one another, to a value of 0 to 100, the sum of w, x and z being greater than 0;
  y corresponds to a value of 1 to 20;
  X is N or O,
  n being 1 if X is O; or n being 2 if X is N; and
  (ii) monomer units of at least one additional copolymerizable comonomer; wherein the seeds are unsown seeds,
  wherein unsown seeds are seeds at any period from the harvest of the seeds to the sowing of the seeds.

2. The method according to claim 1, wherein the polyarylphenol polyalkoxy ether sulfate is the compound having CAS-No. 119432-41-6 or the polyarylphenol polyalkoxy ether phosphate is the compound having CAS-No.176776-21-9.

3. The method of claim 1, wherein the composition comprises at least 0.1% by weight of polyarylphenol polyalkoxy ether phosphate and/or polyarylphenol polyalkoxy ether sulfate and at most 50% by weight of polyarylphenol polyalkoxy ether phosphate and/or polyarylphenol polyalkoxy ether sulfate.

4. The method of claim 2, wherein the ethylenically unsaturated carboxylic acid is acrylic and/or methacrylic acid.

5. The method of claim 2, wherein the alkoxylate residue of the general formula (II) is an ethoxylate residue of the formula (IIa)

$$R^1\text{—O—}(C_2H_4O)_z\text{—} \quad \text{(IIa)}$$

in which
$R^1$ is hydrogen or an aliphatic hydrocarbon residue with 1 to 40 carbon atoms; and
z corresponds to a value of 1 to 100.

6. The method of claim 1, wherein the copolymerizable comonomer is methyl acrylate and/or methyl methacrylate.

7. The method according to claim 1, wherein the copolymer has a weight-average molecular weight of at least 5 kDa.

8. The method of claim 1, wherein the copolymer is the compound having CAS-No. 111 740-36-4.

9. The method according to claim 1, wherein the composition comprises at least 0.1% by weight of copolymer and at most 20% by weight of copolymer.

10. The method of claim 1, wherein the composition further comprises an antifreeze agent.

11. The method of claim 1, wherein the antifreeze agent is glycerin.

12. The method of claim 1, wherein the composition does not comprise a significant amount of a further surfactant having an HLB value of more than 5.

13. The method of claim 1, wherein the composition does not comprise more than 1% by weight of a further surfactant having an HLB value of more than 5.

14. The method of claim 1, wherein the composition does not comprise more than 0.5% by weight of a further surfactant having an HLB value of more than 5.

15. The method of claim 1, wherein the composition is an aqueous suspension concentrate.

16. The method of claim 1, wherein the active ingredient is pyraclostrobin, triticonazole, or combinations thereof.

17. The composition of claim 1, wherein the composition does not comprise a further surfactant having an HLB value of more than 5.

18. The method of claim 1, wherein $R^1$ is hydrogen or an aliphatic hydrocarbon residue with 1 to 40 carbon atoms that is a linear or branched, saturated or unsaturated $C_1$-$C_6$-alkyl.

19. The method of claim 3, wherein the composition comprises at least at least 0.5% by weight of polyarylphenol polyalkoxy ether phosphate and/or polyarylphenol polyalkoxy ether sulfate, and at most 20% by weight of polyarylphenol polyalkoxy ether phosphate and/or polyarylphenol polyalkoxy ether sulfate.

20. The method of claim 3, wherein the composition comprises at least 1% by weight of polyarylphenol polyalkoxy ether phosphate and/or polyarylphenol polyalkoxy ether sulfate and at most 5% by weight of polyarylphenol polyalkoxy ether phosphate and/or polyarylphenol polyalkoxy ether sulfate.

21. The method of claim 5, wherein $R^1$ is hydrogen or an aliphatic hydrocarbon residue with 1 to 40 carbon atoms that is a linear or branched, saturated or unsaturated $C_1$-$C_6$-alkyl.

22. The method of claim 9, wherein the composition comprises at least 0.2% by weight and at most 10% by weight of copolymer.

23. The method of claim 9, wherein the composition comprises at least 1% by weight and at most 3% by weight of copolymer.

24. Seed treated with an active ingredient;
a polyarylphenol polyalkoxy ether phosphate and/or polyarylphenol polyalkoxy ether sulfate having the formula (I):

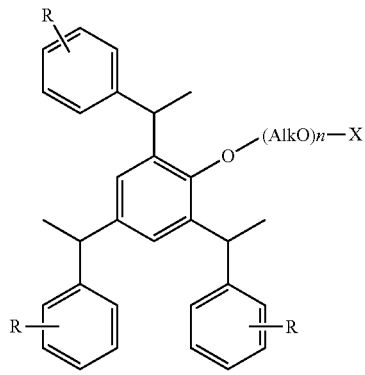

wherein each R independently represents hydrogen or $C_1$-$C_4$ alkyl; Alk represents $C_2$-$C_6$ alkylene; n has a value from 5 to 60; and X is —$SO_3H_2$ or —$PO_3H$; or an agriculturally acceptable base addition salt thereof; and
a copolymer comprising:
(i) monomer units of at least one ester of an ethylenically unsaturated carboxylic acid, wherein the carboxylic acid ester has an alkoxylate residue of the general formula (II):

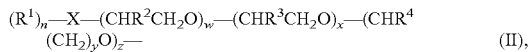

in which
$R^1$ is hydrogen or an aliphatic hydrocarbon residue with 1 to 40 carbon atoms;
$R^2$, $R^3$, $R^4$ are, independently of one another, hydrogen or $C_1$-$C_4$- alkyl;
w, x, z correspond, independently of one another, to a value of 0 to 100, the sum of w, x and z being greater than 0;
y corresponds to a value of 1 to 20;
X is N or O,
n being 1 if X is O; or n being 2 if X is N; and
(ii) monomer units of at least one additional copolymerizable comonomer;
wherein the seed is an unsown seed,
wherein unsown seeds are seeds at any period from the harvest of the seeds to the sowing of the seeds.

* * * * *